United States Patent
Takahashi

(10) Patent No.: US 8,866,897 B2
(45) Date of Patent: *Oct. 21, 2014

(54) IMAGE PICKUP DEVICE AND IMAGE PICKUP METHOD FOR THE SAME

(75) Inventor: Hisashi Takahashi, Tochigi (JP)

(73) Assignee: Honda Motor Co., Ltd., Tokyo (JP)

( * ) Notice: Subject to any disclaimer, the term of this patent is extended or adjusted under 35 U.S.C. 154(b) by 678 days.

This patent is subject to a terminal disclaimer.

(21) Appl. No.: 13/184,056

(22) Filed: Jul. 15, 2011

(65) Prior Publication Data

US 2012/0033068 A1    Feb. 9, 2012

(30) Foreign Application Priority Data

Aug. 6, 2010   (JP) ................................. 2010-177175

(51) Int. Cl.
    *G01N 21/88*    (2006.01)

(52) U.S. Cl.
    CPC ...................................... *G01N 21/88* (2013.01)
    USPC ...................................... 348/92; 348/E7.085

(58) Field of Classification Search
    None
    See application file for complete search history.

(56) References Cited

U.S. PATENT DOCUMENTS

| | | | | |
|---|---|---|---|---|
| 3,799,682 A | * | 3/1974 | Colestock et al. | 356/237.2 |
| 5,135,303 A | * | 8/1992 | Uto et al. | 356/237.2 |
| 5,848,188 A | * | 12/1998 | Shibata et al. | 382/203 |
| 6,741,731 B1 | * | 5/2004 | Yamamoto et al. | 382/141 |
| 2005/0275833 A1 | * | 12/2005 | Silver | 356/237.1 |
| 2006/0038987 A1 | * | 2/2006 | Maeda et al. | 356/237.5 |
| 2007/0058854 A1 | * | 3/2007 | Caskey et al. | 382/152 |
| 2007/0109534 A1 | * | 5/2007 | Shibata et al. | 356/237.5 |
| 2007/0206184 A1 | * | 9/2007 | Uto et al. | 356/237.2 |
| 2010/0149527 A1 | * | 6/2010 | Baran et al. | 356/237.2 |
| 2010/0157055 A1 | * | 6/2010 | Pechatnikov | 348/144 |

FOREIGN PATENT DOCUMENTS

| | | |
|---|---|---|
| JP | 05-231842 A | 9/1993 |
| JP | 2009-052917 A | 3/2009 |

* cited by examiner

*Primary Examiner* — Jayanti K Patel
*Assistant Examiner* — Reza Aghevli
(74) *Attorney, Agent, or Firm* — Rankin, Hill & Clark LLP

(57) ABSTRACT

Image pickup is executed at an image pickup timing based on reference pulses by using, as a trigger, workpiece pulses which are output at an interval synchronized with a shape portion (projecting or recess portion) which is periodically and repetitively formed on a workpiece being rotated, and the image pickup is executed at the image pickup timing based on the reference pulses PA every time only reference pulses PA whose number corresponds to a pulse number between workpiece pulses are output from the image pickup timing concerned.

3 Claims, 5 Drawing Sheets

IMAGE PICKUP DEVICE AND IMAGE PICKUP METHOD FOR THE SAME

INCORPORATION BY REFERENCE

The present application claims priority under 35 U.S.C. §119 to Japanese Patent Application No. 2010-177175 filed on Aug. 6, 2010. The content of the application is incorporated herein by reference in its entirety.

BACKGROUND OF THE INVENTION

1. Field of the Invention

The present invention relates to an image pickup device and an image pickup method that rotate a workpiece having a shape portion containing at least one of a projecting (convex) portion and a recess (concave) portion which is periodically and repetitively formed on the workpiece, and pick up images of the respective shape portions while rotating the workpiece, thereby performing an appearance inspection on the workpiece.

2. Description of the Related Art

There is known an appearance inspecting device for picking up images of a gear as a workpiece fed by a feeding unit and detecting the presence or absence of defects of gear teeth from the pickup images (for example, see JP-A-5-231842). According to this type of appearance inspecting device, a turbine wheel used in a turbocharger for a vehicle engine or the like is freely rotatably supported by a servo motor. The turbine wheel is subjected to step feeding by the servo motor, and the rotation thereof is stopped at an image pickup position, whereby images of all the blades of the turbine wheel can be picked up by a fixedly mounted camera (for example, see JP-A-2009-52917).

It has been desired to pick up images of portions which are periodically and repetitively formed on a workpiece (for example, teeth of a gear, blades of a turbine wheel or the like) and pick up respective images under the same condition (for example, at the same position) when an appearance inspection is executed from the respective pickup images.

However, the appearance inspecting device disclosed in JP-A-2009-52917 has a merit that images of more inspection places can be picked up by rotating the turbine wheel as compared with the appearance inspecting device disclosed in JP-A-5-231842. However, this appearance inspecting device requires a structure and a control operation for stopping a workpiece precisely because the workpiece is step-fed and stopped at a predetermined rotational angle. Furthermore, the turbine wheel is stopped every image pickup and thus much time is required to terminate pickup of all images.

SUMMARY OF THE INVENTION

The present invention has been implemented in view of the foregoing situation, and has an object to provide an image pickup device and an image pickup method that establish synchronization between a motor for rotating a workpiece and an image pickup timing of a portion which is periodically and repetitively formed on a workpiece, whereby nondisruptive image pickup can be implemented.

In order to attain the above object, according to an aspect of the present invention, an image pickup device for rotating a workpiece on which a shape portion containing at least one of a projecting portion and a recess portion is periodically and repetitively formed, and picking up images of the shape portion of the workpiece, comprises: a workpiece rotating mechanism including a motor for rotating the workpiece at a fixed rotational speed, and an encoder that is disposed on a rotational shaft of the motor to output reference pulses at a fixed interval; an image pickup controller for picking up images of the workpiece at an image pickup timing based on the reference pulses while rotating the workpiece; a workpiece pulse output mechanism for outputting workpiece pulses at an interval synchronized with the shape portion of the workpiece being rotated; and a pulse counter for counting an interval between the workpiece pulses on the basis of the reference pulses to obtain a pulse number corresponding to the interval, wherein the image pickup controller performs image pickup at the image timing based on the reference pulses by using the workpiece pulses as a trigger, and performs the image pickup at the image timing based on the reference pulses every time only reference pulses whose number corresponds to the pulse number are output from the image pickup timing.

According to the above image pickup device, the image pickup controller performs image pickup at the image timing based on the reference pulses by using, as a trigger, the workpiece pulses output at the interval synchronized with the shape portion of the workpiece being rotated, and performs the image pickup at the image timing based on the reference pulses every time only reference pulses whose number corresponds to the pulse number between the workpiece pulses are output from the image pickup timing. Therefore, the motor for rotating the workpiece and the image pickup timing for the shape portion which is periodically and repetitively formed on the workpiece can be synchronized with each other, and thus non-stop image pickup can be performed.

In the above image pickup device, the workpiece pulse output mechanism may have a rotator that rotates integrally with the workpiece and has a detection target portion at the same angular interval as the shape portion of the workpiece with respect to the center of the rotation, and a proximity sensor for outputting the workpiece pulses every time the detection target portion of the rotator is detected. Accordingly, the proximity sensor can be disposed away from the workpiece.

The above image pickup device may further comprise a pulse center detection circuit for detecting a pulse width center of each of the workpiece pulses, and the image pickup controller may perform the image pickup at an image pickup timing corresponding to the pulse width center detected by the pulse center detection circuit. Accordingly, the synchronization can be established more precisely.

Furthermore, according to another aspect of the present invention, an image pickup method for rotating a workpiece on which a shape portion containing a projecting portion and a recess portion is periodically and repetitively formed, and picking up images of the shape portion of the workpiece, comprises: a rotating step of rotating the workpiece at a fixed rotational speed by a motor, and outputting reference pulses at a fixed interval from an encoder disposed on a rotational shaft of the motor; a workpiece pulse outputting step of outputting workpiece pulses at an interval synchronized with the shape portion of the workpiece being rotated; a pulse counting step of counting an interval between the workpiece pulses on the basis of the reference pulses to obtain a pulse number corresponding to the interval; and an image pickup step of performing image pickup at an image timing based on the reference pulses by using the workpiece pulses as a trigger, and performing the image pickup at the image pickup timing based on the reference pulses every time only reference pulses whose number corresponds to the pulse number are output from the image pickup timing.

According to the present invention, the image pickup is performed at the image timing based on the reference pulses by using the workpiece pulses as the trigger, and the image pickup at the image timing based on the reference pulses is performed every time only reference pulses whose number corresponds to the pulse number are output from the image pickup timing. Therefore, the motor for rotating the workpiece and the image pickup timing for the shape portion which is periodically and repetitively formed on the workpiece can be synchronized with each other, and thus non-stop image pickup can be performed.

DETAILED DESCRIPTION OF THE PREFERRED EMBODIMENT

A preferred embodiment according to the present invention will be described with reference to the accompanying drawings.

Figure 1:
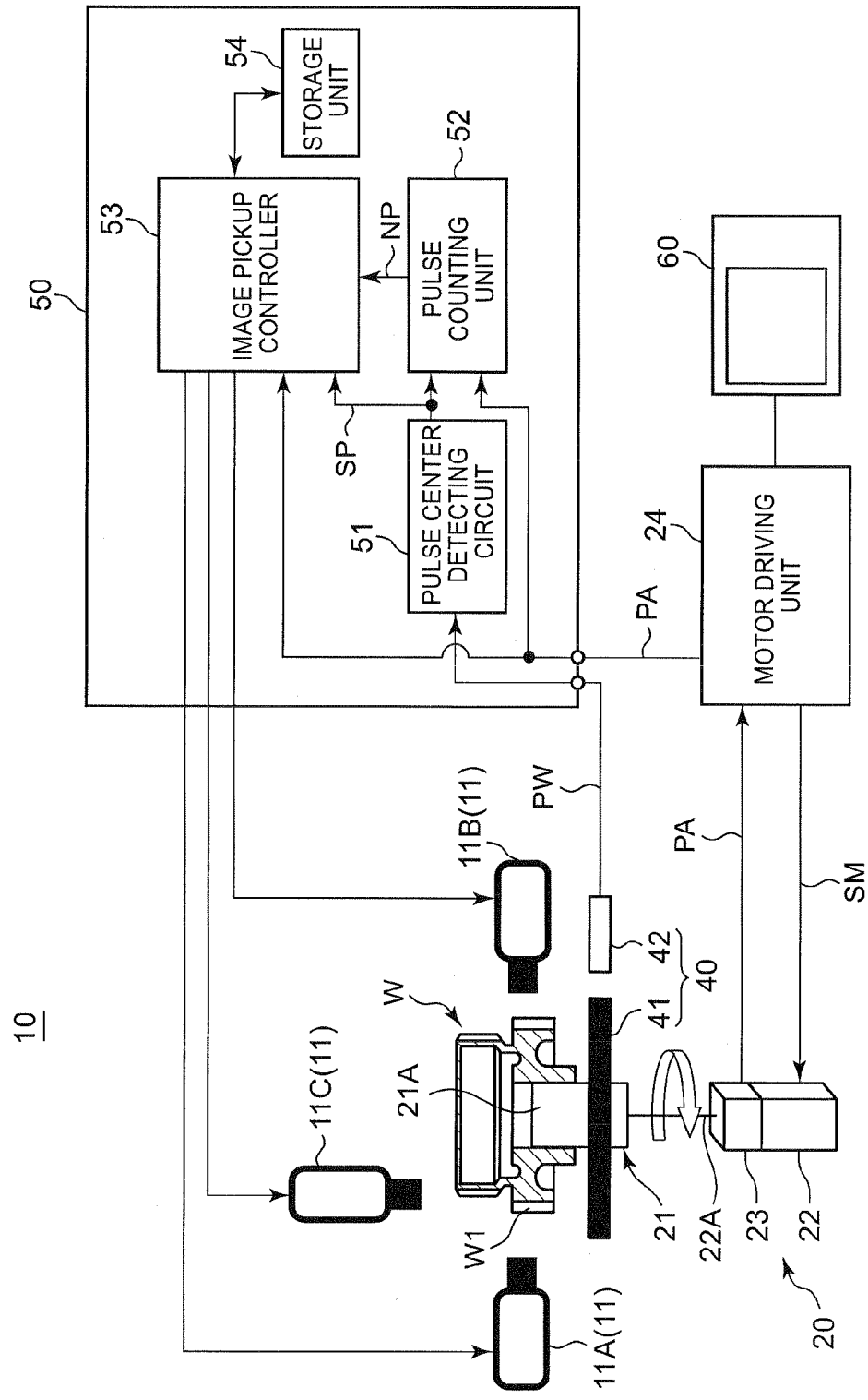
FIG. 1 is a diagram showing an image pickup device for appearance inspection according to an embodiment of the present invention.
Figure 2:
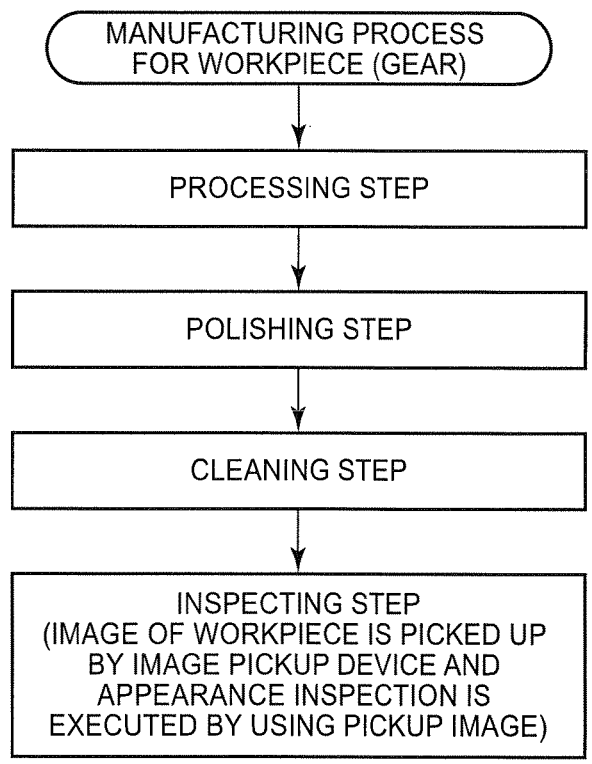
FIG. 2 is a diagram showing a workpiece manufacturing process.

FIG. 1 is a diagram showing an image pickup device for appearance inspection according to an embodiment of the present invention.

This image pickup device 10 is disposed in a manufacturing process for a workpiece W (gear in this embodiment), and it picks up images of the workpiece W manufactured in this manufacturing process by a camera (image pickup unit) 11 to obtain pickup images which are suitable for appearance inspection. Here, the manufacturing process for the workpiece W is performed as follows: processing step of the workpiece W (gear cutting, etc.)→polishing step→cleaning step→inspecting step, and this image pickup device 10 is used in the inspecting step as the final step.

More specifically, after the polishing step of the workpiece W, a worker changes setup and shifts the workpiece W to the cleaning step. After the cleaning step, cleaning liquid is removed from the workpiece W by air blow, and the workpiece W is shifted to the inspection step containing the image pickup processing by the image pickup device while the setup state of the cleaning step is kept. That is, the cleaning step and the inspection step are executed under the same setup state (setting), and the processing time is shortened.

A shown in FIG. 1, the image pickup device 10 has a workpiece rotating mechanism 20 for rotating the workpiece W, an image pickup mechanism 30 for picking up images of the workpiece W being rotated, a pulse output mechanism 40 for outputting a workpiece pulse PW representing the position of each tooth portion W1 (described later with reference to FIG. 3) which is periodically and repetitively formed on the workpiece W, an information processing device 50 for executing various kinds of information processing such as the above control, the inspection processing, etc., and an operating device 60 having a display function which is operated by a worker. The information processing device 50 is constructed by installing a mount board having various kinds of circuits mounted thereon into a personal computer.

The workpiece rotating mechanism 20 has a holder portion 21 to which the workpiece W is fixed, a motor 22 for rotationally driving the holder portion 21, an encoder 23 disposed on the rotational shaft 22A of the motor 22, and a motor driving unit 24.

The holder portion 21 is joined to the rotational shaft 22A of the motor 22, and it is rotated at the same speed as the rotational shaft 22A, whereby the workpiece W is rotated. The holder portion 21 has a shaft portion 21A inserted through a through hole which penetrates through the workpiece W in the axis direction, and a publicly known clamp mechanism (not shown) for clamping the workpiece W concentrically with the shaft portion 21A. The shaft portion 21A is joined to the workpiece W by a key K (see FIG. 3), whereby the shaft portion 21A and the workpiece W are joined to each other through the key so as to rotate integrally with each other.

Here, the workpiece W in this embodiment is a gear wheel used for a transmission of a vehicle. This type of gear wheel is provided with a key groove, and the gear wheel is fixed to the holder portion 21 by using the key groove.

As shown in FIG. 1, a workpiece detecting jig (rotator) 41 which constitutes a part of the pulse output mechanism 40 is fixed to the base end side of the shaft portion 21A (the rotational shaft 22A side of the motor 22).

Figure 3:
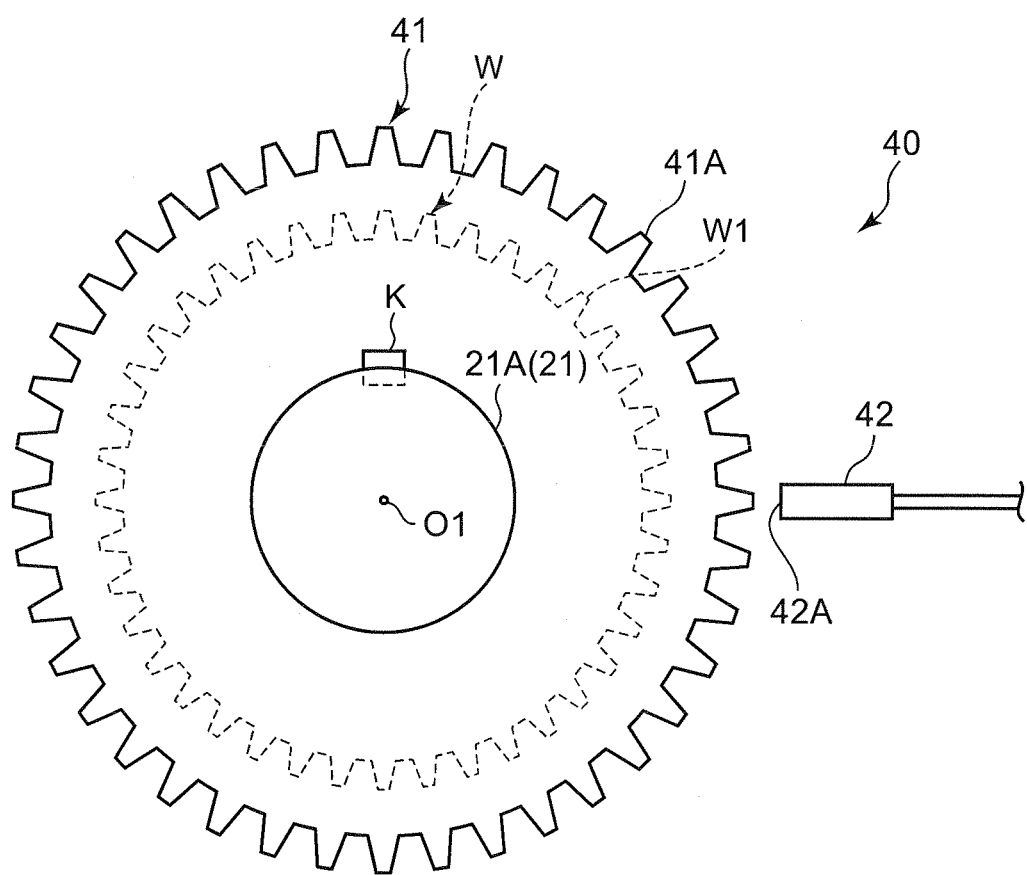
FIG. 3 is a diagram showing both a workpiece detecting jig and a peripheral construction.

FIG. 3 is a diagram showing the workpiece detecting jig 41 together with the peripheral construction thereof.

The workpiece detecting jig 41 is a plate-like member which is fixed to the holder portion 21 and imitates the workpiece W, and the workpiece detecting jig 41 has such a shape that a pseudo tooth portion (pseudo shape portion) which is periodically and repetitively formed on the workpiece detecting jig 41 can be detected by a proximity sensor 42.

More specifically, this workpiece detecting jig 41 is a diameter-increasing part which increases in diameter from the shaft portion 21A with the rotational center O1 of the shaft portion 21A at the center. The workpiece detecting jig 41 is designed as a thin plate having pseudo tooth portions (detection target portions) 41a formed by projecting portions which protrude outwardly in the radial direction and are arranged at an angular interval equal to the pitch of the tooth portions W1 of the workpiece W. In other words, the workpiece detecting jig 41 is designed like a spur wheel whose cross-sectional shape has a similar figure to the side cross-sectional shape of the workpiece W.

The workpiece detecting jig 41 is joined to the shaft portion 21A through a key so as to be rotated integrally with the shaft portion 21A in the neighborhood of the back surface of the workpiece W. Therefore, the workpiece detecting jig 41 functions as a rotator rotating integrally with the workpiece W at a position which is displaced from the workpiece W in the axial direction, but in the neighborhood of the workpiece W.

Furthermore, the pseudo tooth portions 41A of the workpiece detecting jig 41 and the tooth portions W1 of the workpiece W are arranged at the same angular interval with respect to the rotational center O1 of the shaft portion 21A. In this construction, the workpiece detecting jig 41 and the gear-wheel W are joined to each other through the key K as shown in FIG. 3, whereby the pseudo tooth portion 41A of the workpiece detecting jig 41 and the tooth portion W1 of the gear wheel W are aligned with each other in phase.

Furthermore, as shown in the figures, the workpiece detecting jig 41 is formed as a thin plate member, and thus the workpiece detecting jig 41 can be easily disposed by using a base-end side area of the holder portion 21 in which the workpiece W is not mounted.

A servo motor suitable for speed control is used as the motor 22, and under the control of the information processing device 50, the motor 22 is rotationally driven at a fixed rotational speed on the basis of a motor driving signal SM output from the motor driving unit 24.

The encoder 23 is disposed on the rotational shaft 22A of the motor 22, and outputs reference pulses PA whose frequency corresponds to the rotational speed of the rotational shaft 22A. In this construction, the motor 22 is driven at a fixed rotational speed, and thus the encoder 23 outputs reference pulses PA having a fixed frequency.

An encoder for outputting pulses whose number is ten to one hundred times as large as the number of workpiece pulses PW output at the positions of the tooth portions W1 of the workpiece W within the same time is used as the encoder 23, That is, the resolution of the encoder 23 is set so that ten to one hundred pulses (for example, 16 pulses) are output at the rotational angle corresponding to one pitch of the tooth portions W1 of the workpiece W. A rotary encoder is used as the encoder 23.

The reference pulses PA output from the encoder 23 are input to the motor driving unit 24. The motor driving unit 24 executes feed-back control on the motor 22 on the basis of the reference pulses PA to control the rotational speed of the motor 22 to a fixed rotational speed precisely. Furthermore, the reference pulses PA are also input to the information processing device 50 through the motor driving unit 24.

The motor driving unit 24 is constructed by PLC (Programmable Logic Controller) having a motor control function. However, the present invention is not limited to this style, and the motor driving unit 24 may be contained in the information processing device 50.

An operating device 60 having a display function is connected to the motor driving unit 24, and a worker's operation instruction is input to the motor driving unit 24 by operating an operation panel provided to the operating device 60, and the motor driving unit 24 and the information processing device 50 execute various kinds of processing according the operation instruction concerned. Furthermore, the operating device 60 having the display function has a display unit for displaying each kind of information input through the motor driving unit 24.

The pulse output mechanism 40 has the workpiece detecting jig 41 described above, and a single proximity sensor 42 for detecting the pseudo tooth portions 41A of the workpiece detecting jig 41 in a contactless style. As shown in FIG. 3, the proximity sensor 42 is configured so that a sensor portion 42A is disposed so as to face the outer peripheral surface of the workpiece detecting jig 41, and outputs a workpiece pulse PW every time each pseudo tooth portion 41A of the workpiece detecting jig 41 is magnetically detected.

As shown in FIG. 1, the workpiece pulse PW is input to a pulse center detecting circuit 51 in the information processing device 50, and center data SP representing the center of the workpiece pulse PW (corresponding to the pulse width center) is generated by the pulse center detecting circuit 51 and input to a pulse counter 52 and an image pickup controller 53 in the information processing device 50.

The pulse counter 52 counts the pulse number NI (called as a reference pulse number NP) of the reference pulses PA between the centers of continuous workpiece pulses PW to obtain the reference pulse number NP between the workpiece pulses PW, and notifies the reference pulse number NP to the image pickup controller 53.

The image pickup controller 53 controls the operation of the camera 11 so as to pickup images at the imaging timings based on the reference pulses PA. Te reference pulses PA are input to the image pickup controller 53, and the center of the workpiece pulse PW detected by the pulse center detecting circuit 51 and the reference pulse number NP between the workpiece pulse PW which is counted by the pulse counter 52 are notified to the image pickup controller 53.

The image pickup controller 53 is connected to a workpiece image pickup camera 11 through a wire to transmit an image pickup instruction to the camera 11 and also obtain image data picked up by the camera 11.

In the figures, reference numeral 54 represents a storage unit for storing workpiece information such as the image pickup data, the reference pulse number NP, the number of teeth of the workpiece W (the number of shape portions), etc. A computer-readable recording medium such as a magnetic recording medium, an optical recording medium, a semiconductor recording medium or the like is applied as the storage unit 54.

The image pickup controller 53 and the camera 11 constitute an image pickup mechanism 30. In this embodiment, plural cameras (three cameras in this embodiment) are fixedly installed as the camera 11 to pick up images of the tooth portions W1 of the workpiece W under different conditions.

Specifically, as shown in FIG. 1, these cameras 11 contain a camera for picking up an image of a tooth face (the overall surface of the tooth portion W1) (first image pickup unit) 11A, a camera for picking up an image of a tooth tip (the tip of the tooth portion W1) (second image pickup unit) 11B, and an end face image pickup camera for picking up an image of an end face of the tooth portion W1 (third image pickup unit) 11C.

Digital cameras for picking up still images are used as these cameras 11, and have shutter speed performance with which pickup images are not blurred even when the images of the workpiece W being rotated are picked up, a sufficient number of pixels for appearance inspection, and a lens suitable for image pickup of each part. A so-called area camera (which is also called as an area sensor camera) is used as the tooth face image pickup camera 11A, and so-called line cameras (which are also called as line sensor cameras) are used as the tooth tip image pickup camera 11B and the end face image pickup camera 11C.

Figure 4:
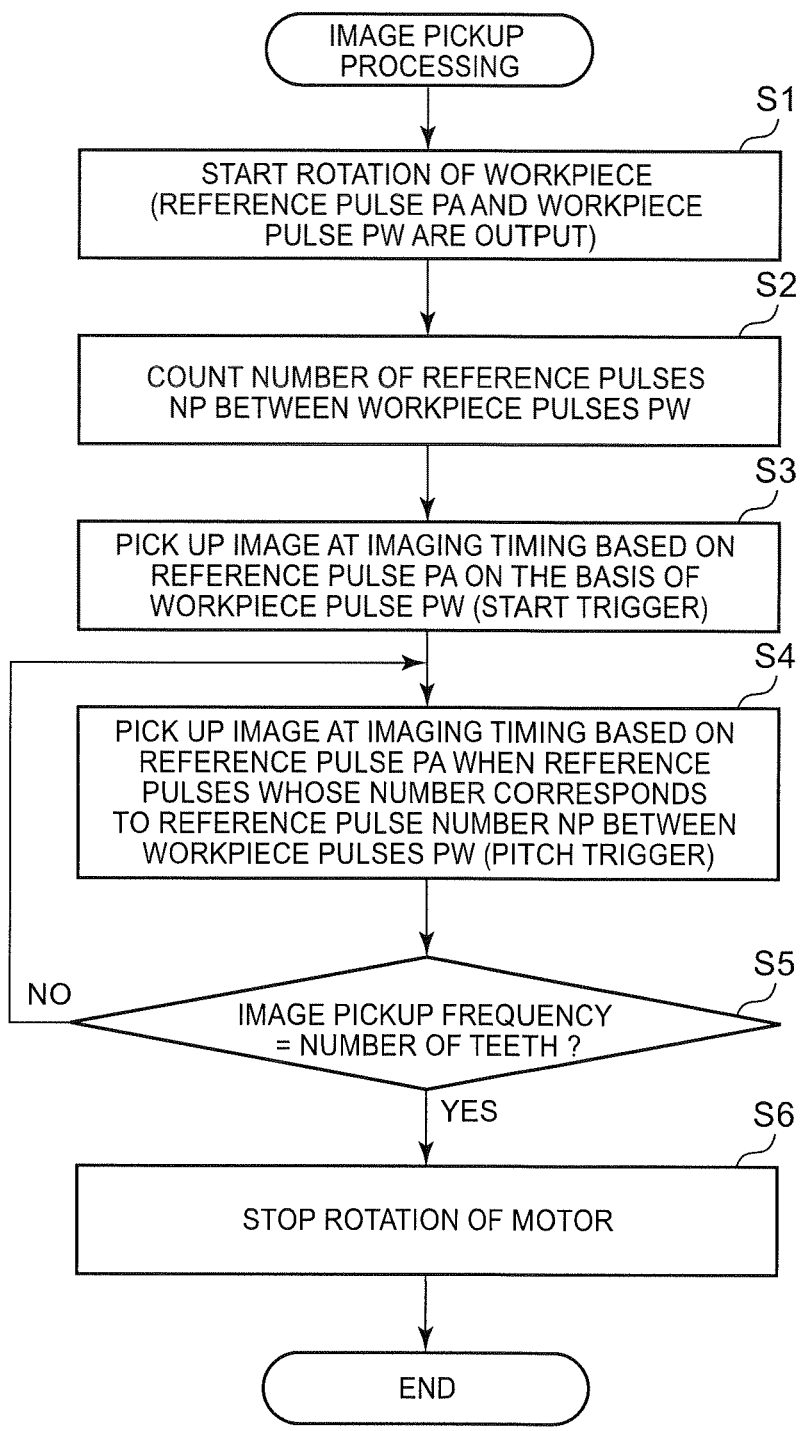
FIG. 4 is a flowchart showing the operation of the image pickup device.

Next, the operation when the image pickup device 10 controls the image pickup of the tooth face image pickup camera 11A will be described. FIG. 4 is a flowchart showing this operation.

First, the image pickup device 10 starts the rotating operation of the motor 22 by the motor driving unit 24 (step S1: start of rotation step). In this case, the motor 22 is controlled to rotate at a preset fixed rotational speed.

When the motor 22 is driven to rotate, the reference pulses PA are output from the encoder 23, and also the workpiece pulses PW are output from the proximity sensor 42 (workpiece pulse output step).

Figure 5:
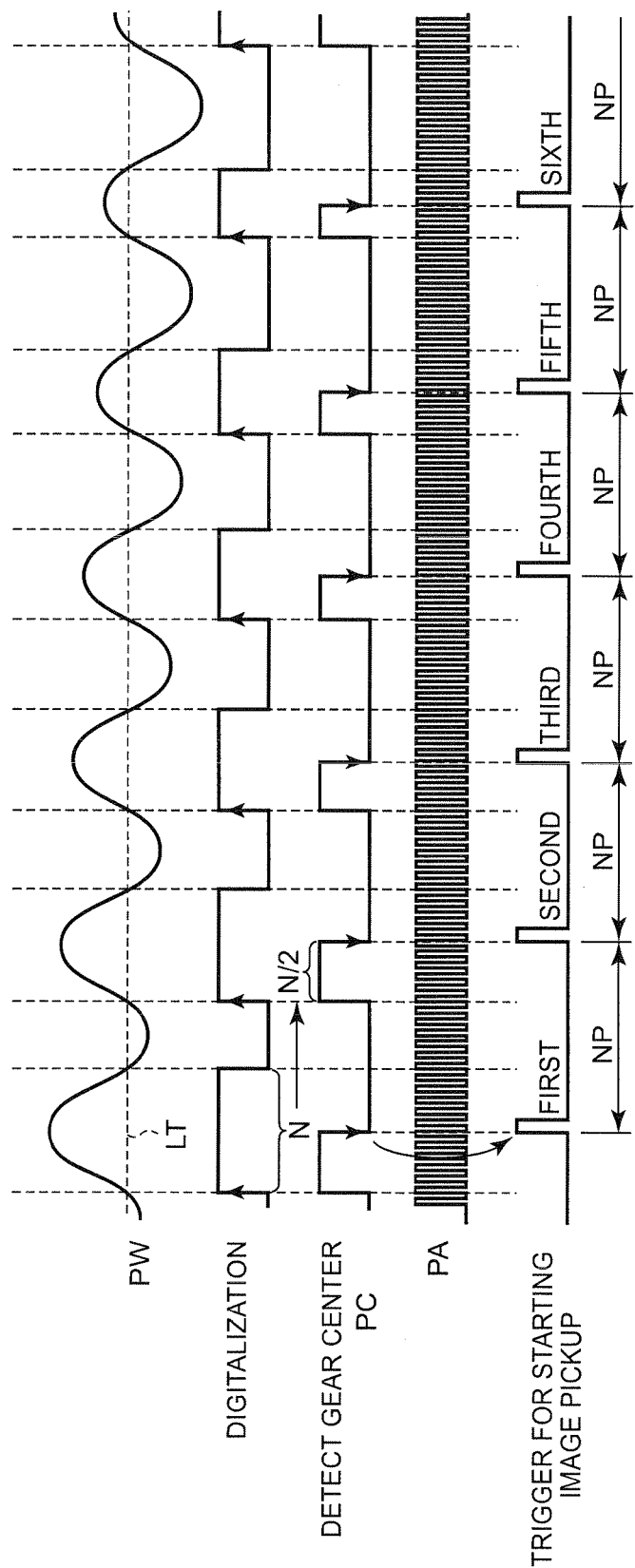
FIG. 5 is a time chart of a pulse output.

The pulse outputs from the encoder 23 and the proximity sensor 42 are obtained as a time chart shown in FIG. 5. As shown in FIG. 5, the proximity sensor 42 generates an output signal voltage having a peak at the center portion thereof (i.e., high-crowned output signal voltage) in the range of a single tooth portion (shape portion) which is periodically and repetitively formed on the workpiece W, and this output signal voltage is digitalized. In FIG. 5, reference character LT represents a threshold level when the workpiece pulses PW are digitalized. The pulse center detecting circuit 51 measures the digitalized pulse width N, generates a half pulse width (N/2) of the measured pulse width N in synchronism with a next pulse rising through an output signal voltage from the proximity sensor 42, and outputs the pulse having the half pulse width (N/2) as a tooth tip center detection pulse PC.

Accordingly, the end edge of the pulse (the tooth tip center detection pulse PC) of the generated pulse width (N/2) corresponds to the center position of the tooth portion W1. Therefore, the pulse number of the reference pulses PA is counted in conformity with the digitalized pulse width N, and the pulse width of the half pulse width (N/2) of this count value is generated, whereby the center of the workpiece pulse PW (the pulse width center), that is, the tooth portion center of the workpiece W is detected.

Furthermore, during this rotation, the reference pulse number NP between the workpiece pulses PW is counted by the pulse counter 52 (step S2: pulse count step), and the processing of the step S3 and subsequent steps (image pickup step) is executed.

In this case, the image pickup controller 53 detects the image pickup timing based on the reference pulse PA by using the workpiece pulse PW as a trigger for starting image pickup (start trigger), and outputs an image pickup trigger signal to the tooth face image pickup camera 11A at this image pickup timing, thereby making the tooth face image pickup camera 11A pick up an image.

At this time, the image pickup controller 53 specifies from the reference pulse PA the image pickup timing corresponding to the center of the workpiece pulse PW detected by the pulse center detecting circuit 51, and performs the image pickup operation at this specified timing. Therefore, the image pickup can be accurately performed at the timing at which the proximity sensor 42 detects the tooth portion center of the workpiece W. The image pickup controller 53 of this embodiment is configured so that any one of the falling edge and rising edge of the reference pulse PA may be selected and used as an image pickup timing (start trigger).

In this embodiment, for a first image pickup operation, the tooth tip center detection pulse PC is set as a trigger for starting image pickup. That is, the image pickup timing is not specified from the reference pulses PA, but the timing of the end edge of the tooth tip center detection pulse PC itself is set as the image pickup timing. Accordingly, the error between the image pickup timing and the timing at which the tooth portion center of the workpiece W is detected by the proximity sensor 42 is minimized.

Subsequently, the image pickup controller 53 determines on the basis of the image pickup timing whether only the reference pulses PA whose number corresponds to the reference pulse number NP are output, and outputs the image pickup trigger signal to the tooth face image pickup camera 11A every time the reference pulse number NP of reference pulses PA are output, thereby making the tooth face image pickup camera 11A pick up an image (step S4).

In this case, the image pickup controller 53 counts an image pickup frequency, and determines whether the counted image pickup frequency is coincident with the number of teeth of the workpiece W. When they are not coincident with each other (step S5: NO), the image pickup processing of the step S4 is executed again. When the counted image pickup frequency is coincident with the number of teeth (step S5: YES), the rotation of the motor 22 is stopped (step S6), and the image pickup processing is finished.

That is, with respect to the second and subsequent image pickup operations, the image pickup trigger signal is output to the tooth face image pickup camera 11A on the basis of the reference pulses PA from the encoder 23, whereby image pickup can be precisely performed at a fixed interval. According to this embodiment, the image pickup timing for the first image pickup is not specified from the reference pulse PA. However, the present invention is not limited to this style, and the image pickup timing may be also specified from the reference pulses PA for the first image pickup.

As described above, the image pickup operation is carried out at the interval of the workpiece pulses PW, and thus the image pickup operation can be executed in synchronism with the tooth portion (shape portion) W1 of the actual workpiece W. Accordingly, images of the tooth faces corresponding to the contours of the same tooth portions W1 are continuously picked up in the visual field of the tooth face image pickup camera 11A, and thus images of the respective tooth portions W1 which are picked up under the same condition (at the same position) can be obtained. In addition, the image pickup frequency is set to the number of the teeth of the workpiece W, and thus when all the tooth portions W1 are subjected to image pickup at the same position, the image pickup operation can be automatically finished. Furthermore, with respect to the first image pickup operation, the image pickup operation is executed by using, as a trigger, the tooth tip center detection pulse PC generated on the basis of the workpiece pulse PW, and with respect to the second and subsequent image pickup operations, the image pickup operations are executed at a fixed interval by using the reference pulse PA from the encoder 23 as a trigger. Therefore, the error of the image pickup timing can be reduced The fine adjustment of the image pickup position of each tooth portion W1 can be performed by fine adjustment of the position of the tooth face image pickup camera 11A or by correcting the output timing of the image pickup trigger signal by only a minute time.

The data of these pickup images are accumulated in the storage unit 54 provided to the information processing device 50, and the presence or absence of a defect is determined by a publickly known defect detecting function based on image processing which is provided to the information processing device 50. The determination result is notified to the external through the information processing device 50 and the operating device 60 having the display function.

This defect detection is performed by applying a method of searching a defect on the surface of the tooth face (for example, black scale or scratch) on the basis of the comparison with "a surface image of a tooth face of a non-defective product which is picked up in advance" or "a surface image of a tooth face adjacent to a tooth face whose surface image is currently picked up", whereby appearance inspection of the workpiece W is executed.

As described above, according to the forming process of this embodiment, the position of the tooth portion (shape portion) W1 of the workpiece W being rotated is detected by the proximity sensor 42 through the workpiece detecting jig 41, and image pickup is executed at the image pickup timing based on the reference pulses PA by using, as a trigger, the workpiece pulses PW which are output from the proximity sensor 42 at the interval synchronized with the tooth portions W1. The image pickup is executed at the image pickup timing based on the reference pulses PA every time the reference pulses PA whose number corresponds to the reference pulse number NP between the workpiece pulses PW are output from the image pickup timing concerned. Therefore, the image pickup can be executed on the basis of the reference pulses PA at the motor 22 side in conformity with the tooth portion W1 of the actual workpiece W.

Accordingly, the motor 22 for rotating the workpiece W and the image pickup timing of the shape portion which is periodically and repetitively formed on the workpiece W can be synchronized with each other, and thus non-stop image pickup can be implemented. Accordingly, the time required for image pickup for appearance inspection can be shortened.

Furthermore, in this embodiment, the positions of the tooth portions W1 of the workpiece W being rotated are detected by the proximity sensor 42 through the workpiece detecting jig 41. Therefore, the proximity sensor 42 can be disposed away from the workpiece W. Therefore, the proximity sensor 42 and the camera 11 for picking up images of the tooth portions W1 can be disposed away from each other. Therefore, it is easy to install these elements.

In addition, even when there are many kinds of gear wheel parts constituting the workpiece W, the workpiece detecting jig 41 can be shared to workpieces W having the same number of teeth. Furthermore, for workpieces W having a different number of teeth, the image pickup can be easily performed by replacing the workpiece detecting jig 41 with another one.

Furthermore, according to this embodiment, the pulse center detecting circuit for detecting the pulse width center of the workpiece pulse PW is provided, and the image pickup controller 53 controls the image pickup operation so that image pickup is performed at the image pickup timing corresponding to the pulse width center detected by the pulse center detecting circuit 51. Therefore, the synchronization can be more precisely established.

The present invention is not limited to the above embodiment, and various modifications may be made without departing from the subject matter of the present invention. For example, in the above embodiment, the workpiece detecting jig 41 is provided, however, the present invention is not limited to this style. For example, the workpiece detecting jig 41 may be omitted, and the proximity sensor 42 may directly detect the tooth portions (shape portions) W1 of the workpiece W.

Furthermore, in the above embodiment, the gear wheel is applied as the workpiece W, however, the present invention is not limited to this style. For example, parts other than the gear wheel such as a turbine wheel, a screw or the like may be applied as the workpiece W. In short, the present invention is broadly applied to an image pickup device for a workpiece W on which a shape portion such as a projecting portion such as a tooth, a blade (vane) or the like or a recess portion recessed inwardly is periodically and repetitively formed.

What is claimed is:

1. An image pickup device for rotating a workpiece on which a shape portion containing at least one of a projecting portion and a recess portion is periodically and repetitively formed, and picking up images of the shape portion of the workpiece, comprising:
    a workpiece rotating mechanism including a motor for rotating the workpiece at a fixed rotational speed, and an encoder that is disposed on a rotational shaft of the motor to output reference pulses at a fixed interval;
    an image pickup controller for picking up images of the workpiece at an image pickup timing based on the reference pulses while rotating the workpiece;
    a workpiece pulse output mechanism for outputting workpiece pulses at an interval synchronized with the shape portion of the workpiece being rotated; and
    a pulse counter for counting an interval between the workpiece pulses on the basis of the reference pulses to obtain a pulse number corresponding to the interval,
    wherein the workpiece pulse output mechanism has a rotator that is formed separately from the workpiece, rotates integrally with the workpiece and has a detection target portion at the same angular interval as the shape portion of the workpiece with respect to the center of the rotation, and a proximity sensor for outputting the workpiece pulses every time the detection target portion of the rotator is detected, and
    the image pickup controller performs image pickup at the image timing based on the reference pulses by using the workpiece pulses as a trigger, and performs the image pickup at the image timing based on the reference pulses every time only reference pulses whose number corresponds to the pulse number are output from the image pickup timing.

2. The image pickup device according to claim 1, further comprising a pulse center detection circuit for detecting a pulse width center of each of the workpiece pulses, wherein the image pickup controller performs the image pickup at an image pickup timing corresponding to the pulse width center detected by the pulse center detection circuit.

3. An image pickup method for rotating a workpiece on which a shape portion containing a projecting portion and a recess portion is periodically and repetitively formed, and picking up images of the shape portion of the workpiece, comprising:
    a rotating step of rotating the workpiece at a fixed rotational speed by a motor, and outputting reference pulses at a fixed interval from an encoder disposed on a rotational shaft of the motor;
    a workpiece pulse outputting step of outputting workpiece pulses every time a detection target portion of a rotator is detected, the rotator being formed separately from the workpiece and rotating integrally with the workpiece, and the detection target portion being provided to the rotator at the same angular interval as the shape portion of the workpiece with respect to the center of the rotation;
    a pulse counting step of counting an interval between the workpiece pulses on the basis of the reference pulses to obtain a pulse number corresponding to the interval; and
    an image pickup step of performing image pickup at an image timing based on the reference pulses by using the workpiece pulses as a trigger, and performing the image pickup at the image pickup timing based on the reference pulses every time only reference pulses whose number corresponds to the pulse number are output from the image pickup timing.

* * * * *